United States Patent [19]
Xie

[11] Patent Number: 5,977,199
[45] Date of Patent: Nov. 2, 1999

[54] COMPOSITION, DELIVERY SYSTEM THEREFOR, AND METHOD FOR MAKING TEMPORARY CROWNS AND BRIDGES

[75] Inventor: Xiaoyi Xie, San Gabriel, Calif.

[73] Assignee: The Kerr Corporation, Orange, Calif.

[21] Appl. No.: 09/024,858

[22] Filed: Feb. 17, 1998

[51] Int. Cl.[6] ................................. C08F 2/46; C08F 2/00; B65D 25/08
[52] U.S. Cl. .................................. 522/8; 522/13; 522/14; 522/24; 522/28; 522/48; 522/168; 522/182; 522/184; 522/908; 526/65; 526/66; 526/78; 526/82; 526/83; 526/217; 526/227; 206/219; 206/220; 206/568
[58] Field of Search ..................................... 522/8, 13, 14, 522/24, 28, 48, 168, 182, 184, 908; 526/65, 66, 78, 82, 83, 217, 227; 206/219, 220, 545, 568

[56] References Cited

U.S. PATENT DOCUMENTS

| | | | |
|---|---|---|---|
| 4,602,076 | 7/1986 | Ratcliffe et al. | 522/7 |
| 4,674,980 | 6/1987 | Ibsen et al. | 433/228.1 |
| 4,746,686 | 5/1988 | Waller | 522/14 |
| 5,033,650 | 7/1991 | Colin et al. | 222/137 |
| 5,091,441 | 2/1992 | Omura | 523/109 |
| 5,376,691 | 12/1994 | May et al. | 522/77 |
| 5,554,665 | 9/1996 | Tateosian et al. | 522/30 |

OTHER PUBLICATIONS

*Principles of Polymerization*, G. Odian, pp. 242–251, (1981).
*New Amine Accelerators for Composite Restorative Resins*, G.M. Brauer et al., J Dent Res 58(10): 1994–2000, Oct. 1979.

*Primary Examiner*—Nathan M. Nutter
*Attorney, Agent, or Firm*—Wood, Herron & Evans, L.L.P.

[57] ABSTRACT

The invention describes a dental composition, delivery system and method for making temporary crowns and bridges in which the composition comprises two free-radical polymerizable pastes, one a catalyst paste and the other a base paste, wherein the catalyst paste comprises at least one polymerizable monomer, at least one polymerization initiator which is a peroxide oxidizing agent, at least one first polymerization inhibitor and a filler, and wherein the base paste comprises at least one polymerizable monomer, at least one polymerization accelerator, at least one second polymerization inhibitor, at least one non-polymerizable plasticizer and a filler. These catalyst and base pastes are stored in a dual cartridge from which they can be dispensed with a dispenser, preferably in a 1:1 volume ratio, and can be mixed in a static mixer to form a moldable polymerizing material, which is then applied to a prepared area of one or more teeth in a patient's mouth to form a crown or a bridge. The materials produced in this way have improved handling properties and exhibit a reduced oxygen inhibited layer on the surface of the cured material.

46 Claims, No Drawings

COMPOSITION, DELIVERY SYSTEM THEREFOR, AND METHOD FOR MAKING TEMPORARY CROWNS AND BRIDGES

FIELD OF THE INVENTION

This invention relates to a dental material, delivery system therefor, and method for making temporary crowns and bridges.

BACKGROUND OF THE INVENTION

Materials for use in making temporary and provisional crowns and bridges, are generally divided into two forms: powder/liquid and paste/paste; two mixing techniques: hand spatulation and automixing; and two curing systems: self-cured and light-cured. Temporary crowns and bridges and provisional crowns and bridges are used pending placement of a permanent crown or bridge in a patients mouth. Those useful for up to three months are often referred to as temporary crowns and bridges while those useful for up to one year are sometimes referred to as provisional crowns and bridges.

The powder/liquid form has been widely used in the past, particularly those containing monofunctional monomers. Typically, the powder component comprises polymers such as poly(methyl methacrylate) mixed with dibenzoyl peroxide. The liquid component comprises plasticizer and monomers such as methyl methacrylate and/or butyl methacrylate. The paste/paste form, developed mainly in the last decade, is usually comprised of multifunctional monomers filled with polymer or glass fillers.

The hand spatulation and mixing technique used in the past has a disadvantage in that it introduce numerous air bubbles into the mixed pastes. The entrapped air bubbles in the hardened material are detrimental to physical strength and lead to sites for bacterial colonies and discoloration. Furthermore, it is very difficult to measure out the proper small quantities needed to mix the components in a desired mixing ratio using this technique.

In very recent years, the automixing technique has become the preferred method for mixing the paste/paste materials. In this technique, the paste materials are individually stored in separate chambers of automix cartridges. When they are to be used, the pastes are automatically mixed and dispensed from their individual chambers and through a static mixer. A static mixer typically has a mixing chamber enclosing a stationary mixing member that causes the individual streams of paste from the cartridge chambers to combine, divide, recombine and mix. Components are extruded from their respective cartridges or cartridge chambers into the mixing chamber in predetermined ratios. The components mix as they pass through the mixing chamber and out an outlet. The ratios are determined by the configurations of the cartridges from which the components are extruded into the mixer.

PROTEMP GARANT by ESPE Dental-Medizin GmbH, Seefeld/Oberbay., Germany, TURBOTEMP by Danville Materials (San Ramon, Calif.) and ULTRA TRIM by Bosworth Co. (Skokie, Ill.) are commercially available cartridges for polymerization mixing in a 1:4 volume ratio of catalyst and base pastes, respectively. LUXATEMP by DMG Hamburg, Germany and INTEGRITY by Dentsply/Caulk (Milford, Del.) are commercially available cartridges for polymerization mixing in a 1:10 volume ratio of catalyst and base pastes, respectively. May et al. in U.S. Pat. No. 5,376,691 discloses two admixable pastes for making temporary crowns and bridges in a volume ratio between 1:5 and 1:20. The U.S. Pat. No. 5,376,691 does not disclose the use of a polymerization inhibitor and contains a polymerizable monomer in the base paste only. Tateosian et al in U.S. Pat. No. 5,554,665 discloses a method and dispenser for making a denture reline. Tateosian employs two pastes of similar viscosities that can be mixed in a volume ratio of 1:1 to 1:5, each past containing a polymerizable monomer and a single polymerization inhibitor such as butylated hydroxytoluene. The entire disclosures of U.S. Pat. Nos. 5,376,691 and 5,554,665 are hereby respectfully incorporated herein by reference.

Prior art temporary crown and bridge materials produced by mixing catalyst and base pastes from a cartridge, in a volume ratio other than 1:1, such as between 1:4 and 1:20, have drawbacks on usage. Most dentists have a delivery system in a 1:1 ratio for dispensing other dental materials, such as impression materials. Dispensing two pastes in ratios other than 1:1 requires a delivery system that is designed in that other desired single predetermined ratio. Therefore, dentists have to either purchase an extra delivery system or change the plunger that is used to push pastes out of the cartridge following the dispensing of an impression material. The first case is not economical and creates the need for added storage space and more time for disinfecting, since there are two systems instead of one. The second case is inconvenient in practice.

It is also typical in prior art methods to mix two liquids or two pastes with the same or similar viscosities in static mixers. The catalyst paste, however, has substantially different Theological characteristics than the base paste. As a result, where the base paste and catalyst paste have the same viscosity, the catalyst paste initially moves through the mixer at a faster rate than the base paste, causing unmixed catalyst paste to appear first at the outlet of the mixer. This causes non-uniform and incomplete curing in portions of the dispensed mixture.

The prior art materials, such as those disclosed in U.S. Pat. No. 5,554,665 produced by mixing two free radical polymerizable acrylic pastes, have a thick oxygen (air) inhibited layer (smear layer) on the surface of the cured materials. An oxygen inhibited layer is a layer of uncured paste in which polymerization is inhibited by oxygen dissolved in the paste from the atmosphere. Such layers cannot be fully avoided in free radical polymerizations. A thick oxygen inhibited layer causes a very sticky surface which creates difficulty in handling and which must be cleaned with alcohol. Furthermore, unreacted monomers in the oxygen inhibited layer may be toxic and cause skin sensitivity.

Ratcliffe et al in U.S. Pat. No. 4,602,076 discloses the use of an organic peroxide in a photopolymerizable dental adhesive composition comprising a ketone photoinitiator that improves cure on irradiation with visible light at ambient temperature and in the presence of air. The U.S. Pat. No. 4,602,076 does not employ polymerization inhibitors.

SUMMARY OF THE INVENTION

The present invention provides a dental material for making temporary and provisional crowns and bridges, particularly temporary crowns and bridges, comprised of a catalyst paste and a base paste that can be mixed in a static mixer to form a moldable polymerizing material that exhibits improved handling properties and a reduced oxygen inhibited layer on the surface of the cured material. Unless the context otherwise requires, both temporary and provisional crowns and bridges are generically referred to herein as temporary crowns and bridges.

In the dental material of the present invention, the catalyst paste is comprised of at least one polymerizable acrylic monomer, at least one polymerization initiator, at least one polymerization inhibitor and filler. The base paste is comprised of at least one polymerizable acrylic monomer, at least one polymerization accelerator, at least one polymerization inhibitor, and filler.

Preferably, the catalyst paste and the base paste are each comprised of at least one polymerizable multifunctional acrylic monomer, with at least one polymerizable acrylic monomer in the catalyst paste being different than a monomer of the base paste. Preferably also, the at least one polymerization initiator is preferably an oxidizing agent, and preferably a peroxide oxidizing agent, and the at least one polymerization accelerator is preferably a reducing agent. Additionally, at least one non-polymerizable plasticizer is preferably included in one of the pastes, particularly the base paste.

Furthermore, in preferred embodiments of the invention, at least two different polymerization inhibitors are present in the material. Preferably, one of the pastes, preferably the base paste, includes two different polymerization inhibitors. One type of polymerization inhibitor may be included in both pastes. Preferably, two different polymerization inhibitors are selected to respectively provide two different functions, one to influence gel time, for example, to lie in the range of from one to two minutes from the time the pastes are first mixed, and one to influence set time, for example to lie in a range of from one to two minutes beyond the point at which the material has gelled.

In addition, in a preferred embodiment of the invention, there is provided a dental material for making temporary crowns and bridges comprised of a catalyst paste and a base paste in which the base paste contains a relatively large amount of polymerization accelerator, for example in the base paste, of from approximately two to six times the amount normally regarded as the maximum desirable amount. Preferably, the accelerator is accompanied with a proportional amount of polymerization inhibitor and a decreased amount of polymerization initiator in the catalyst paste.

In accordance with other aspects of the present invention, a dental material is provided for making temporary crowns and bridges that comprises two free radical polymerizable pastes: a catalyst paste and a base paste, wherein the viscosity of the catalyst paste is greater than the viscosity of the base paste. Still further, the two pastes are preferably separately stored in different chambers of a dual cartridge where they can be dispensed with a handheld dispenser and mixed in a static mixer. Moreover, the pastes of the preferred embodiment of the present invention are capable of being dispensed in approximately a 1:1 volume ratio and are provided in a dual chamber cartridge that provides for dispensing in an approximately 1:1 volume ratio.

In accordance with yet another aspect of the present invention, a method of making temporary crowns and bridges is provided comprising the steps of: 1) providing a redox free-radical polymerization system having a catalyst paste and a base paste wherein the catalyst paste comprises at least one polymerizable acrylic monomer, at least one polymerization initiator, at least one polymerization inhibitor and filler, and wherein the base paste comprises at least one polymerizable acrylic monomer, at least one polymerization accelerator, at least one polymerization inhibitor, and filler; and 2) mixing the catalyst and base pastes, preferably from a dual chamber cartridge through a static mixer to form a polymerizing material. The method preferably also includes the steps of 3) applying the polymerizing material directly to a premade impression; and 4) molding the polymerizing material within a prepared area of one or more teeth in a patient's mouth to form a crown or a bridge. Preferably also, the catalyst paste comprises at least one polymerizable monomer, at least one polymerization initiator which is a peroxide oxidizing agent, at least one polymerization inhibitor and a filler, and the base paste comprises at least one polymerizable monomer, at least one polymerization accelerator, at least one polymerization inhibitor, at least one non-polymerizable plasticizer and a filler.

In accordance with the present invention, there is thus provided a dental material for making temporary crowns and bridges comprised of two radical polymerizable pastes that a) may be mixed in a 1:1 volume ratio in a static mixer, b) exhibits short set times coupled with long gel times due to the use of multiple inhibitors, c) does not sacrifice shelf stability, and d) results in only a minimum oxygen inhibited layer on the surface.

These and other objects and advantages of the present invention shall become more apparent from the accompanying description of the preferred embodiments of the invention and the examples.

DETAILED DESCRIPTION

In the present invention, the catalyst paste comprises at least one polymerizable acrylic monomer, at least one polymerization initiator, at least one polymerization inhibitor, and filler.

Polymerizable monomers useful in accordance with the principles of the present invention are (meth)acrylate-functional monomers such as ethylene glycol di(meth)acrylate, diethylene glycol di(meth)acrylate, triethylene glycol di(meth)acrylate, tetraethylene glycol di(meth)acrylate, neopentyl glycol di(meth)acrylate, 1,3-butanediol di(meth)acrylate, 1,6-hexanediol di(meth)acrylate, trimethylolpropane tri(meth)acrylate, 2,2-bis[4-(2-hydroxy-3-acryloyloxypropoxy)phenyl]propane, 2,2-bis[4-(2-hydroxy-3-methacryloyloxypropoxy)phenyl]propane (popular name: Bis-GMA), 2,2-bis[4-(acryloyloxy-ethoxy)phenyl]propane, 2,2-bis[4-(methacryloyloxy-ethoxy)phenyl]propane, urethane di(meth)acrylate, and the like. The term "(meth) acrylate" herein means either methacrylate or acrylate. Among the above-listed monomers, the 2,2-bis[4-(methacryloyloxy-ethoxy)phenyl]propane (popular name: ethoxylated bisphenol-A-dimethacrylate) is the preferred monomer for use in the catalyst paste. One or more polymerizable monomers may be used in the catalyst paste.

Polymerization initiators can be chosen from known organic peroxides such as dibenzoyl peroxide, di-p-chlorobenzoyl peroxide, di-2,4-dichlorobenzoyl peroxide, tertiary butyl peroxybenzoate, methyl ethyl ketone peroxide, ditertiary butyl peroxide, dicumyl peroxide and cumene hydroperoxide, and the like. A suitable and preferred peroxide is dibenzoyl peroxide. A suitable amount of the dibenzoyl peroxide added is in the range from about 0.3 to about 1.7% by weight. One or more polymerization initiators may be used in the catalyst paste.

Polymerization inhibitors for use in the catalyst paste include butylated hydroxytoluene, hydroquinone, hydroquinone monomethyl ether, benzoquinone, chloranil, phenol, and the like. A preferred first polymerization inhibitor for use in the catalyst paste is butylated hydroxytoluene, particularly where ethoxylated bisphenol-A-dimethacrylate is used as the monomer. The inhibitor is used to scavenge small amounts of free radicals during storage and to improve the shelf stability of the paste. The effectiveness of the particular inhibitor used will depend on such things as the type of monomer used in the paste, the presence of other components, and the quantities of the various other components present in the past. One skilled in the art may determine which inhibitors would be useful in the particular paste composition being used. A number of known inhibitors, their characteristics, and their compatibility with various monomer systems are discussed in G. Odian, Principles of Polymerization p242–251 (1981), which is incorporated herein by reference. More than one inhibitor may also be used in the catalyst paste.

Fillers useful in the paste compositions of the invention include organic and inorganic fillers. Organic fillers are particulate polymers or copolymers. Inorganic fillers are silicon dioxide and glasses. A preferred silicon dioxide is submicron amorphous fumed silica, preferably treated with a silane or polymer to improve hydrophobicity. Fumed silica's thixotropic characteristics greatly improve the thickness and stackability of the paste and allow easy extrusion through a static mixer. The glass fillers include borosilicate glass, barium glass, strontium glass, yttrium glass, zirconium glass, lanthanum glass, and the like. A preferred glass filler is barium glass, which provides good radiopacity. Preferably, the glass filler has a particle size of less than 200 microns, most preferably in the range of about 0.1 to about 10 microns. Further, the filler is preferably treated with a silane such as gamma-methacryloxy propyl trimethoxy silane (trade name A-174 manufactured by Union Carbide, Danbury, Conn.) to improve bonding between the filler and the polymer matrix. Other silanes can also be substituted for this purpose.

In the present invention, the base paste comprises at least one polymerizable monomer, at least one polymerization accelerator, at least one polymerization inhibitor, at least one non-polymerizable plasticizer, and filler.

The polymerizable monomers listed for use in the catalyst paste may also be useful in the base paste provided that a different monomer is used in each paste. A preferred polymerizable monomer in the base paste is urethane dimethacrylate (UDMA). A small amount of Bis-GMA is also preferably added as a second monomer to improve curing and therefore reduce the oxygen inhibited layer and increase the flexural strength of the cured material.

Polymerization accelerators must be used in combination with a peroxide to allow rapid polymerization of the monomer at room temperature. One skilled in the art will appreciate that tertiary amines are generally preferred for use in dental restoratives, as described in an article by G. M. Brauer et al. in 58 Journal of Dental Research 1994–2000 (1956), which is incorporated herein by reference. One skilled in the art will also appreciate that known tertiary amines or newly synthesized tertiary amines may be used. Typical tertiary amines include triethanol amine, N,N,3,5-tetramethyl aniline, 4-(dimethylamino)-phenethyl alcohol, dimethyl aminobenzoic acid ester, dimethyl-p-toluidine, dihydroxyethyl-p-toluidine, and the like. A preferred amine accelerator for use in the present invention is dihydroxyethyl-p-toluidine. A suitable amount of dihydroxyethyl-p-toluidine is in the range from 2% to 5% by weight. In a base composition in which less than 2% by weight of dihydroxyethyl-p-toluidine and in a catalyst composition in which less than 0.3% by weight of dibenzoyl peroxide have been added, the curing of the mixture is not satisfactory. In a base composition in which less than 2% by weight of dihydroxyethyl-p-toluidine and in a catalyst composition in which 0.3% to 1.7% by weight of dibenzoyl peroxide have been added, the oxygen inhibited layer on the surface of the cured material is too thick or too sticky. On the other hand, if the amount of dihydroxyethyl-p-toluidine exceeds 6% by weight of the base composition, the shelf life of the paste decreases, and the cured material tends to be yellow in color.

Suitable polymerization inhibitors in the base paste can be selected from the list described for the catalyst paste. Preferably, at least one inhibitor used in either the catalyst or base paste is different from another inhibitor used in one of the pastes, preferably in the other paste. Furthermore, at least one of the pastes preferably contains at least two different polymerization inhibitors. In the preferred embodiment of the invention, acceptable polymerization gel time, set time and paste shelf stability are observed where multiple inhibitors are used in either the catalyst paste or base paste, and preferably in the base paste. The preferred inhibitors in the base paste are a combination of butylated hydroxytoluene and hydroquinone monomethyl ether. Both inhibitors act as a scavenger to trap free radicals and to extend gel time, setting time and paste shelf stability. However, hydroquinone monomethyl ether has a greater influence on gel time and butylated hydroxytoluene has a greater influence on setting time. As a result, hydroquinone monomethyl ether extends the gel time without unduly extending the set time, which would be the case with butylated hydroxytoluene used alone in increased amounts. The incorporation of different amounts of two different inhibitors will produce the desired gel time and setting time. One skilled in the art will appreciate that the particular type or types and quantities of inhibitors used in the system to produce desired gel and set times will depend upon the particular types and quantities of monomers and other components present in the system.

A non-polymerizable plasticizer is also preferably included, and can be chosen from saturated or inert liquid organic compounds including alkylphthalates, liquid paraffins and low-molecular-weight polyglycols. Examples are diethyl phthalate, dibutyl phthalate, mineral oil, poly (ethylene glycol)-Mn 200–400, poly(propylene glycol)-Mn 400–4000 and the like, where Mn refers to the number average molecular weight. Preferred non-polymerizable plasticizers are dibutyl phthalate and/or poly(propylene glycol)-Mn 4000. One or more non-polymerizable plasticizers may also be added to the catalyst paste.

The filler for the base paste can be selected from the same list of fillers used in the catalyst paste or from among other fillers. A different filler can be utilized in the catalyst paste than in the base paste.

A photoinitiator and a promoter may be added to either the catalyst paste or base paste to make the material light-curable. In this case, it is necessary that the paste compositions be stored in an opaque container, typically a black container. Camphorquinone is a typical photoinitiator used in dental materials. Other suitable photoinitiators and promoters are described in U.S. Pat. No. 4,746,686, which is incorporated herein by reference.

For aesthetic or other purposes, the paste compositions may include small quantities of additives such as pigments, opalescent agents, fluorescent agents, ultraviolet stabilizers, anti-oxidants and the like provided that they do not substantially affect cure.

In a general preferred embodiment in accordance with the present invention, the catalyst paste and base paste comprise the compositions in the following approximate ranges of proportions by weight:

| | WT. % |
|---|---|
| CATALYST PASTE | |
| Ethoxylated bisphenol-A-dimethacrylate | 0–75 |
| Bis-GMA | 0–75 |
| Urethane dimethacrylate | 0–75 |
| Triethylene glycol dimethacrylate | 0–75 |
| Poly(propylene glycol)-Mn 4000 | 0–20 |
| Dibenzoyl peroxide | 0.3–1.7 |
| Butylated hydroxytoluene | 0–0.5 |
| Hydroquinone monomethyl ether | 0–0.1 |
| Fumed silica | 0–10 |
| Barium glass, silanized | 0–60 |
| BASE PASTE | |
| Ethoxylated bisphenol-A-dimethacrylate | 0–75 |
| Bis-GMA | 0–75 |
| Urethane dimethacrylate | 0–75 |
| Triethylene glycol dimethacrylate | 0–75 |
| Dibutyl phthalate | 0–20 |
| Dihydroxyethyl-p-toluidine | 2–6 |
| Camphorquinone | 0–2 |
| Butylated hydroxytoluene | 0–0.5 |
| Hydroquinone monomethyl ether | 0–0.1 |
| Fumed silica | 0–10 |
| Barium glass, silanized | 0–60 |
| Additives | 0–0.5 |

In a preferred embodiment of the present invention, both the catalyst and base paste compositions are stored in a non-contact state, in separate chambers of a dual cartridge described in U.S. Pat. No. 5,554,665, which is incorporated herein by reference. A polymerizing material is produced by extruding the catalyst paste and base paste through a static mixer attached to the dual cartridge. Both the catalyst paste and base paste can be mixed in a volume ratio between 1:1 and 1:2 or between 1:1 and 2:1. Preferably, the catalyst paste and base paste are mixed in a substantially 1:1 volume ratio. The polymerization catalyst is activated when the catalyst and base pastes are mixed. The mixed paste starts polymerizing in less than 3 minutes from the beginning of mixing. The viscosity of the mixed paste increases gradually. Within less than 6 minutes from the beginning of mixing, the polymerizing paste is hardened. Preferably, the catalyst paste and base paste are mixed bubble-free and yield bubble-free cured materials with strong physical properties. Cured materials made in accordance with this embodiment of the present invention have a minimum thickness (less than 50 $\mu$m) of oxygen inhibited layer on the surface.

In another preferred embodiment of the present invention, the viscosity of the catalyst paste in accordance with the invention is substantially greater than the viscosity of the base paste. While prior art methods typically mixed two liquids or pastes with the same or similar viscosities in the static mixers, the nature of the materials used in accordance with the present invention dictates that the catalyst paste be of a thicker consistency than the base paste in order to use a 1:1 dispensing system. The rheological characteristics of the catalyst paste are substantially different than those of the base paste. It was found that the initial mixture does not cure if the viscosities of the catalyst paste and base paste are the same or similar because the catalyst paste tends to come out of a static mixer faster than the base paste. A more satisfactory mixing and uniform curing can be obtained only when the catalyst paste is adjusted to be thicker than the base paste, such that the pastes are extruded at the same or similar rate. Increasing the filler content, preferably the fumed silica content, in the catalyst paste will result in a thicker paste, since certain filler components such as fumed silica are highly sensitive to viscosity.

The compositions of the present invention are advantageously used for making temporary crowns and bridges. Two polymerizable pastes, a catalyst paste and a base paste, are mixed from a dual cartridge in a static mixer to form a polymerizing material which is then extruded directly onto a premade impression or a plastic matrix. Afterwards the impression or matrix, including the polymerizing material, is immediately applied to an area of one or more prepared teeth in a patient's mouth. The polymerizing material is molded by pressing the impression or plastic matrix. Within minutes, the polymerizing material is partially polymerized and hardened. In a preferred embodiment, the impression or plastic matrix including the molded partially polymerized material is removed from the patient's mouth before the polymerizing material is hardened, and is further polymerized extraorally at ambient temperature to substantially complete the cure. In another embodiment of the present invention, the partially polymerized material after molding is further cured by irradiating the molded material in a patient's mouth with light from a light curing apparatus. In another embodiment of the present invention, the partially polymerized material after molding is removed from the patient's mouth and is further cured in a heat curing oven. Alternatively, the partially polymerized material after molding is removed from the patient's mouth and is further cured by irradiating the molded material in a light curing oven, which provides both heat and light.

The current invention overcomes the deficiencies of auto-mixing systems for mixing catalyst paste and base paste in a volume ratio other than 1:1, such as between 1:4 and 1:20, and provides a convenient usage of dispensing pastes from a dual cartridge in a static mixer to make temporary crowns and bridges. The current invention employs multiple inhibitors in the paste compositions and overcomes the deficiencies of the self-cured systems by enabling similar set times coupled with longer gel times, while preserving their shelf stability. The system of this invention offers the best handling properties, such as satisfactory mixing, curing and a minimum thickness oxygen inhibited layer (less than 50 $\mu$m) on the surface of cured materials.

EXAMPLE 1

The following example illustrates a preferred embodiment of the present invention.

TABLE 1

| | WT. % |
|---|---|
| CATALYST PASTE | |
| Ethoxylated bisphenol-A-dimethacrylate | 55.88 |
| Dibenzoyl peroxide | 1.0 |
| Butylated hydroxytoluene | 0.12 |
| Fumed silica | 5.0 |
| Barium glass, silanized | 38.0 |
| BASE PASTE | |
| Bis-GMA | 5.0 |
| Urethane dimethacrylate | 41.42 |
| Dibutyl phthalate | 10.0 |
| Dihydroxyethyl-p-toluidine | 4.4 |
| Butylated hydroxytoluene | 0.06 |
| Hydroquinone monomethyl ether | 0.01 |
| Fumed silica | 3.0 |
| Barium glass, silanized | 36.0 |
| Pigment | 0.11 |

Both the catalyst paste and base paste were separately formed by mixing the ingredients in a planetary mixer. The catalyst paste had a consistency number of 2.9 cm and the base paste had a consistency number of 4.7 cm. The consistency number was determined by measuring the diameter of 1.0 gram of paste that had been placed between two flat and leveled glass slides and pressed under a weight of 108.0 grams for ten minutes. The catalyst paste and base paste were stored in the separate chambers of a 50 ml dual cartridge (CS050-01-09) made by MixPac Systems AG, Rotkreuz, Switzerland. This cartridge was then placed in a hand-held dispenser made by MixPac. A static mixer was attached to the cartridge. The catalyst and base pastes were extruded in a 1:1 volume ratio from the static mixer and directly applied into a premade impression or matrix which was immediately placed on a prepared tooth. After about two minutes, the impression with the curing material was removed. The obtained crown was allowed to cure for an additional two minutes. After trimming and polishing a temporary crown was formed.

EXAMPLE 2

The following example illustrates the comparison of the gel time and set time for the base paste of Example 1 having dual polymerization inhibitors and a base paste having a single polymerization inhibitor.

TABLE 2

| BASE PASTE with single inhibitor | WT. % |
|---|---|
| Bis-GMA | 5.0 |
| Urethane dimethacrylate | 41.43 |
| Dibutyl phthalate | 10.0 |
| Dihydroxyethyl-p-toluidine | 4.4 |
| Butylated hydroxytoluene | 0.06 |
| Fumed silica | 3.0 |
| Barium glass, silanized | 36.0 |
| Pigment | 0.11 |

The base paste with single inhibitor was formed by mixing the ingredients in Table 2 in a planetary mixer. The catalyst paste was formed as described in Example 1. The catalyst paste and base paste were stored in the separate chambers of a 50 ml dual cartridge made by MixPac (CS 050-01-09). This cartridge was then placed in a hand-held dispenser made by MixPac. A static mixer was attached to the cartridge. The catalyst and base pastes were extruded in a 1:1 volume ratio from the static mixer. The gel times and set times are shown in Table 3 for the pastes of Examples 1 and 2, which contain two and one polymerization inhibitors in the base paste, respectively. The gel time was measured as the time it takes from the initial mixing of the pastes for the material to no longer peak up from the surface when probed by a hand-held sharp instrument. The set time was measured as the period of time during which the hand-held probe is capable of penetrating the surface of the material.

TABLE 3

| Samples | Gel Time (Seconds) | Set Time (Seconds) |
|---|---|---|
| Material of Example 1 | 90 | 140 |
| Material of Example 2 | 40 | 90 |

The results in Table 3 show a significant difference in the gel time between the base paste having a single polymerization inhibitor and the one having two polymerization inhibitors. Although the set time is slightly longer in the material of Example 1, this is acceptable so long as the longer gel time is achieved. Preferably, the gel time is in the range of from approximately one to two minutes of the initial mixing of the pastes while the set time is from approximately one to two longer than the gel time from the initial mixing of the pastes.

EXAMPLE 3

The following example illustrates similar viscosities (consistencies) of catalyst and base pastes, which resulted in unsatisfactory curing of the initial mixture.

TABLE 4

|  | WT. % |
|---|---|
| CATALYST PASTE |  |
| Ethoxylated bisphenol-A-dimethacrylate | 58.83 |
| Dibenzoyl peroxide | 1.0 |
| Butylated hydroxytoluene | 0.17 |
| Fumed silica | 3.0 |
| Barium glass, silanized | 37.0 |
| BASE PASTE |  |
| Bis-GMA | 5.0 |
| Urethane dimethacrylate | 41.08 |
| Dibutyl phthalate | 10.0 |
| Dihydroxyethyl-p-toluidine | 3.8 |
| Hydroquinone monomethyl ether | 0.01 |
| Fumed silica | 4.0 |
| Barium glass, silanized | 36.0 |
| Pigment | 0.11 |

Both catalyst paste and base paste were separately formed by mixing the ingredients in a planetary mixer. The catalyst paste had a consistency number of 3.6cm and the base paste had a consistency number of 3.9 cm. The viscosities of catalyst and base pastes were very similar. The catalyst paste and base paste were stored in the separate chambers of a 50 ml dual cartridge made by MixPac (CS 050-01-09). This cartridge was then placed in a hand-held dispenser made by MixPac. A static mixer was attached to the cartridge. The catalyst and base pastes were extruded in a 1:1 volume ratio from the static mixer, preferably at room temperature. In this system, the initial mixture of catalyst and base pastes contains mostly catalyst paste composition and hence does not polymerize for a prolonged period of time. The catalyst paste of Example 1 had a substantially lower consistency number than the base paste due to the higher fumed silica content, and as a result, satisfactory curing of the initial mixture was achieved.

EXAMPLE 4

The following example illustrates that the use of the higher dihydroxyethyl-p-toluidine level of 4.4 wt % in Example 1 attains a thinner oxygen inhibited layer than the use of the lower dihydroxyethyl-p-toluidine level of this example.

TABLE 5

|  | WT. % |
|---|---|
| CATALYST PASTE |  |
| Ethoxylated bisphenol-A-dimethacrylate | 55.18 |
| Dibenzoyl peroxide | 1.7 |
| Butylated hydroxytoluene | 0.12 |
| Fumed silica | 5.0 |
| Barium glass, silanized | 38.0 |

TABLE 5-continued

| BASE PASTE | WT. % |
|---|---|
| Bis-GMA | 5.0 |
| Urethane dimethacrylate | 43.99 |
| Dibutyl phthalate | 10.0 |
| Dihydroxyethyl-p-toluidine | 0.9 |
| Fumed silica | 4.0 |
| Barium glass, silanized | 36.0 |
| Pigment | 0.11 |

Both the catalyst paste and base paste were separately formed by mixing the ingredients in a planetary mixer. The catalyst paste and base paste were stored in the separate chambers of a 50 ml dual cartridge made by MixPac (CS 050-01-09). This cartridge was then placed in a hand-held dispenser made by MixPac. A static mixer was attached to the cartridge. The catalyst and base pastes were extruded in a 1:1 volume ratio through the static mixer. The thickness of the oxygen inhibited layer is shown in Table 6 for the pastes of Examples 1 and 4, which contain different amounts of dihydroxyethyl-p-toluidine in the base paste. The thickness of the oxygen inhibited layer was determined by measuring the thickness of the uncured layer of paste, which had been placed between two flat microscope glass slides spaced 0.15 mm under a microscope. The thickness of the oxygen inhibited layer for existing temporary crown and bridge materials is also represented in Table 6.

TABLE 6

| Samples | Mixing volume ratio of catalyst and base | Oxygen inhibited layer (μm) |
|---|---|---|
| Material of Example 1 | 1:1 | 40 |
| Material of Example 4 | 1:1 | 50 |
| Protemp Garant, ESPE | 1:4 | 40 |
| Turbotemp, Danville Materials | 1:4 | 53 |
| Ultra Trim, Bosworth | 1:4 | 59 |
| Luxatemp, DMG Hamburg | 1:10 | 50 |

It can be seen that the material of Example 1 is the only 1:1 ratio system that observes an oxygen inhibited layer of less than 50 μm. Protemp Garant also observes a minimum oxygen inhibited layer, but employs a 1:4 ratio system, and therefore, lacks the other benefits of the 1:1 ratio system of Example 1. Thus, adjusting the viscosity of the catalyst paste in conjunction with increasing the amount of accelerator in the base paste results in a minimum oxygen inhibited layer in a 1:1 ratio system.

EXAMPLE 5

The following example in comparison with Example 1 illustrates the role of polymerization inhibitors in extending the shelf life of the catalyst paste and base paste.

TABLE 7

| CATALYST PASTE | WT. % |
|---|---|
| Ethoxylated bisphenol-A-dimethacrylate | 55.53 |
| Dibenzoyl peroxide | 1.3 |
| Butylated hydroxytoluene | 0.17 |

TABLE 7-continued

| | WT. % |
|---|---|
| Fumed silica | 5.0 |
| Barium glass, silanized | 38.0 |
| BASE PASTE | |
| Bis-GMA | 5.0 |
| Urethane dimethacrylate | 42.89 |
| Dibutyl phthalate | 10.0 |
| Dihydroxyethyl-p-toluidine | 3.0 |
| Fumed silica | 3.0 |
| Barium glass, silanized | 36.0 |
| Pigment | 0.11 |

Both the catalyst paste and base paste were separately formed by mixing the respective ingredients of each in a planetary mixer. The catalyst paste and base paste were stored in the separate chambers of a 50 ml dual cartridge made by MixPac (CS 050-01-09). The shelf life test was performed by storing the filled cartridges having a plug closing one end at selected temperatures. At certain time intervals, the cartridge was removed from the oven and cooled to 23° C. The plug was removed from both cylinders, and a pointed probe (150 mm by 1 mm diameter) was inserted into the paste to check for polymerization. Shelf life at each temperature is the time from initial formulation of the paste to just before polymerization is first detected. Acceptable dental materials of this type generally have a shelf life at 42° C. exceeding 21 days. The shelf life is shown in Table 8 for the pastes of Examples 1 and 5. The results show that the shelf life at 42° C. in the paste with the higher dihydroxyethyl-p-toluidine level (Example 1) is extended by incorporation of inhibitors in both catalyst and base pastes. However, in the catalyst and base paste system of Example 5, which does not contain any inhibitor in the base paste, has far less shelf stability of the base paste at 42° C. Further in the system of Example 5, with the higher amount of catalyst or initiator in the catalyst paste that is needed to compensate for lack of accelerator in the base paste, even with a proportional increase in inhibitor in the catalyst paste, the shelf stability of the catalyst paste is also decreased.

TABLE 8

| Samples | Shelf life at 42° C. | Shelf life at 50° C. |
|---|---|---|
| Catalyst paste of Example 1 | >65 days | 40 hrs |
| Catalyst paste of Example 5 | 6 days | 24 hrs |
| Base paste of Example 1 | >65 days | 7 days |
| Base paste of Example 5 | 20 days | 1 day |

The above description and examples demonstrate that the presence of a polymerizable monomer in both pastes and a slightly high filler content in the catalyst paste allows for a 1:1 ratio system with satisfactory curing. Furthermore, increasing the accelerator content in the base paste decreases the thickness of the oxygen inhibited layer. This may, however, cause instability in the mixture. To maintain high stability, a polymerization inhibitor is present in both pastes and dual polymerization inhibitors are present in at least one of the pastes, preferably the base paste. This inhibitor system also serves to increase the gel time of the mixture.

While the present invention has been illustrated by the description of embodiments thereof, and while the embodiments have been described in considerable detail, it is not intended to restrict or in any way limit the scope of the appended claims to such detail. In particular, certain materials may be replaced with materials now or hereafter discovered that provide the functions set forth herein, and changes in components may require corresponding changes to quantities and proportions for replacement components that are equivalent to those recited for the components recited. Additions and modifications will readily appear to those skilled in the art. For example, the viscosities of the pastes may be adjusted to work in a system for dispensing in a 2 to 1 or 1 to 2 ratio. The invention in its broader aspects is therefore not limited to the specific details, representative apparatus and method and illustrative examples shown and described. Accordingly, departures may be made from such details without departing from the scope or spirit of applicant's general inventive concept.

What is claimed is:

1. A delivery system for delivering material for making temporary crowns and bridges, the system comprising:
   a cartridge having two material storage chambers, including a first chamber and a second chamber, the cartridge being configured to expel material simultaneously from each of the chambers in a predetermined volume ratio into a static mixer;
   the first chamber being prefilled with a catalyst paste including at least one polymerizable acrylic monomer, at least one polymerization initiator, a first polymerization inhibitor, and filler; and
   the second chamber being prefilled with a base paste including at least one polymerizable acrylic monomer, at least one polymerization accelerator, a second polymerization inhibitor, a third polymerization inhibitor, and filler; and
   wherein the second polymerization inhibitor is different than the third polymerization inhibitor.

2. The system of claim 1 wherein the first and second polymerization inhibitors are the same.

3. The system of claim 1 wherein the catalyst paste includes a forth polymerization inhibitor which is different than the first polymerization inhibitor.

4. The system of claim 1, wherein the catalyst paste further comprises at least one non-polymerizable plasticizer.

5. The system of claim 4, wherein the non-polymerizable plasticizer is selected from the group consisting of: dibutyl phthalate, polypropylene glycol-Mn 4000 and mixtures thereof.

6. The system of claim 1, wherein one of the pastes further comprises at least one photoinitiator.

7. The system of claim 6, wherein the photoinitiator is camphorquinone.

8. The system of claim 1, wherein the polymerizable acrylic monomer in the catalyst paste is one or more materials selected from the group consisting of: ethoxylated bisphenol-A-dimethacrylate and 2,2-bis[4-(2-hydroxy-3-methacryloyloxypropoxy)phenyl]propane.

9. The system of claim 1, wherein the polymerization initiator is a peroxide oxidizing agent.

10. The system of claim 9, wherein the peroxide oxidizing agent is dibenzoyl peroxide present at a concentration in the range of from about 0.3% to about 1.7% by weight.

11. The system of claim 1, wherein the first polymerization inhibitor is butylated hydroxytoluene.

12. The system of claim 1, wherein the polymerizable acrylic monomer in the base paste is one or more materials selected from the group consisting of: urethane dimethacrylate, 2,2-bis[4-(2-hydroxy-3-methacryloyloxypropoxy)phenyl]propane and mixtures thereof.

13. The system of claim 1, wherein the polymerization accelerator is a tertiary amine.

14. The system of claim 13, wherein the polymerization accelerator is dihydroxyethyl-p-toluidine.

15. The system of claim 14, wherein the dihydroxyethyl-p-toluidine has a concentration in the range of from approximately 2% to approximately 6% by weight.

16. The system of claim 15, wherein the second polymerization inhibitor is butylated hydroxytoluene.

17. The system of claim 16, wherein the third polymerization inhibitor is hydroquinone monomethyl ether.

18. The system of claim 1, wherein the non-polymerizable plasticizer is selected from the group consisting of: alkylphthalates, liquid paraffins and low-molecular-weight polyglycols.

19. The system of claim 18, wherein the base paste includes a non-polymerizable plasticizer selected from the group consisting of: dibutyl phthalate, polypropylene glycol-Mn 4000 and mixtures thereof.

20. The system of claim 1, wherein the filler is one or more materials selected from the group consisting of: fumed silica, barium glass, borosilicate glass, strontium glass, yttrium glass, zirconium glass, and lanthanum glass.

21. The system of claim 1, wherein the catalyst paste has a viscosity greater than the viscosity of the base paste.

22. The system of claim 1, wherein the accelerator is present in an amount effective to achieve an oxygen inhibited layer on the surface of the material after curing of less than 50 µm.

23. The system of claim 1 wherein:
   the viscosity of the catalyst paste is greater than the viscosity of the base paste; and
   the polymerization accelerator is present in an amount effective to achieve an oxygen inhibited layer on the surface of the material after curing of less than 50 µm.

24. A delivery system for delivering material for making temporary crowns and bridges, the system comprising:
   a cartridge having two material storage chambers, including a first chamber and a second chamber, the cartridge being configured to expel material simultaneously from each of the chambers in a predetermined volume ratio into a static mixer;
   the first chamber being prefilled with a catalyst paste including at least one polymerizable acrylic monomer, at least one polymerization initiator, at least one polymerization inhibitor, and filler; and
   the second chamber being prefilled with a base paste including at least one polymerizable acrylic monomer, at least one polymerization accelerator, at least one polymerization inhibitor, and filler; and
   wherein the catalyst paste has a viscosity greater than the viscosity of the base paste such that the initial flow of the catalyst paste through the mixer corresponds to the initial flow of the base paste through the mixer in accordance with the predetermined volume ratio.

25. The system of claim 24 wherein the at least one polymerization inhibitor in the base paste includes one inhibitor that has a greater influence on gel time than setting time and another that has a relatively greater influence on setting time than on gel time.

26. The system of claim 24 wherein the at least one polymerization inhibitor in the base paste includes two different polymerization inhibitors.

27. The system of claim 24, wherein the cartridge is configured to expel material simultaneously from each of the chambers in a predetermined volume ratio of substantially 1 to 1.

28. The system of claim 24, wherein the chambers of the cartridge are each respectively prefilled with approximately equal volumes of the catalyst and base pastes.

29. The system of claim 24, wherein the cartridge has a coupling configured to connect to the inlet end of a static mixer, and each chamber has an outlet positioned to communicate with the inlet end of the mixer when the cartridge is coupled thereto.

30. The system of claim 24 wherein the at least one polymerization accelerator is present in an amount sufficient to achieve an oxygen inhibited layer of not more than 50 microns when the material is cured.

31. The system of claim 30 wherein the at least one polymerization inhibitor in the base paste includes one polymerization inhibitor that, in combination with another polymerization inhibitor in the material, extends the gel time of the material to approximately from one to two minutes from the mixing of the pastes.

32. The material of claim 24 wherein the amount of filler in the catalyst paste is sufficient to raise the viscosity thereof to greater than the viscosity of the base paste.

33. The material of claim 25 wherein the combination of the two polymerization inhibitors in the base paste are effective to provide a gel time of from approximately one to approximately two minutes from the mixing of the pastes with a set time of from approximately one to approximately two minutes from gelling of the material.

34. The system of claim 24 wherein the at least one polymerization inhibitor in the base paste produces a relatively long gel time and a relatively short set time.

35. The system of claim 24 wherein the inhibitor in the catalyst paste and the inhibitor in the base paste achieve a set time of approximately one to two minutes from the mixing of the material.

36. The system of claim 35, wherein the catalyst paste and the base paste each contain a single inhibitor.

37. The system of claim 36 wherein the inhibitor in the catalyst paste is the same as the inhibitor in the base paste.

38. The system of claim 37 wherein the inhibitor in the catalyst paste and the inhibitor in the base paste are both butylated hydroxytoluene.

39. The system of claim 1 wherein the polymerization accelerator is a reducing agent.

40. The system of claim 1, wherein the base paste further comprises at least one non-polymerizable plasticizer.

41. The system of claim 40, wherein the non-polymerizable plasticizer is selected from the group consisting of: dibutyl phthalate, polypropylene glycol-Mn 4000 and mixtures thereof.

42. A delivery system for delivering material for making temporary crowns and bridges, the system comprising:
a cartridge having two material storage chambers, including a first chamber and a second chamber, the cartridge being configured to expel material simultaneously from each of the chambers in a predetermined volume ratio into a static mixer;
the first chamber being prefilled with a catalyst paste including at least one polymerizable acrylic monomer, at least one polymerization initiator, a polymerization inhibitor, and filler; and
the second chamber being prefilled with a base paste including at least one polymerizable acrylic monomer, at least one polymerization accelerator, a polymerization inhibitor, a non-polymerizable plasticizer, and filler; and
wherein the catalyst paste has a viscosity greater than the viscosity of the base paste, and
the set time of the material is approximately one to two minutes from the mixing of the material.

43. The system of claim 42 wherein the inhibitor in the catalyst paste is the same as the inhibitor in the base paste.

44. The system of claim 43 wherein the inhibitor in the catalyst paste and the inhibitor in the base paste are both butylated hydroxytoluene.

45. The system of claim 42 wherein the accelerator is present in an amount effective to achieve an oxygen inhibited layer on the surface of the material after curing of less than 50 $\mu$m.

46. The system of claim 45 wherein the initiator is a peroxide oxidizing agent and the accelerator is a reducing agent.

* * * * *

UNITED STATES PATENT AND TRADEMARK OFFICE
CERTIFICATE OF CORRECTION

PATENT NO : 5,977,199
DATED : November 2, 1999
INVENTOR(S) : Xiaoyi Xie

It is certified that error appears in the above-identified patent and that said Letters Patent are hereby corrected as shown below:

Column 2, line 31 reads "Theological" and should read --rheological--.

Column 8, line 63 reads "Bariurn glass" and should read --Barium glass--.

Claim 16, line 1 reads "claim 15" and should read --claim 1--.

Signed and Sealed this

Twenty-second Day of May, 2001

Attest:

NICHOLAS P. GODICI

Attesting Officer

Acting Director of the United States Patent and Trademark Office